United States Patent [19]
Slishman

[11] Patent Number: 6,117,146
[45] Date of Patent: Sep. 12, 2000

[54] VASCULOPATH

[75] Inventor: Samuel H. Slishman, Albuquerque, N. Mex.

[73] Assignee: The University of New Mexico, Albuquerque, N. Mex.

[21] Appl. No.: 09/332,011

[22] Filed: Jun. 14, 1999

[51] Int. Cl.⁷ .................................................. A61B 17/08
[52] U.S. Cl. ........................................ 606/151; 604/116
[58] Field of Search .................................. 606/151, 150, 606/205–208, 210; 604/115, 116

[56] References Cited

U.S. PATENT DOCUMENTS

| | | |
|---|---|---|
| D. 340,113 | 10/1993 | Knoblauch et al. . |
| 2,704,071 | 3/1955 | Becker . |
| 3,324,854 | 6/1967 | Weese . |
| 4,223,673 | 9/1980 | Harris . |
| 4,403,987 | 9/1983 | Gottinger . |
| 4,586,924 | 5/1986 | Lanning . |
| 4,634,429 | 1/1987 | Schoettley . |
| 4,917,677 | 4/1990 | McCarthy ................................ 606/151 |
| 5,147,306 | 9/1992 | Gubich . |
| 5,242,453 | 9/1993 | Gubich . |
| 5,254,095 | 10/1993 | Harvey . |
| 5,312,350 | 5/1994 | Jacobs . |
| 5,415,647 | 5/1995 | Pisarik . |
| 5,464,413 | 11/1995 | Siska et al. ................................ 606/151 |
| 5,911,707 | 6/1999 | Wolvek et al. ........................... 604/116 |

*Primary Examiner*—Michael Buiz
*Assistant Examiner*—Kevin Truong
*Attorney, Agent, or Firm*—Jagtiani & Associates

[57] ABSTRACT

The present invention provides an adjustable vasculopath device for holding a blood vessel prior to the insertion of medical devices such as needles or intravenous tubes into the blood vessel. The vasculopath device includes a pair of probes which may be inserted intradermally to hold the blood vessel. The present invention also provides a method for holding a blood vessel using two probes inserted intradermally.

7 Claims, 3 Drawing Sheets

VASCULOPATH

BACKGROUND OF THE INVENTION

1. Field of the Invention

The present invention relates generally to medical clamps.

2. Description of the Prior Art

The piercing of blood vessels, namely arteries and veins, is necessary at times for obtaining specimens for analysis, administration of fluids and medications, transfusion of blood, etc. It takes a considerable amount of skill to be able to locate the conduit, immobilize it, and then insert a needle or intravenous tube so as to minimize patient discomfort.

There are multiple problems inherent in this procedure. These conduits, especially veins, are difficult to hold steady. They tend to "roll" (move laterally) when a needle or tube is inserted. If the needle or tube does get inserted into the vein, the vein may collapse. If the needle is inserted and then advanced, the needle may go through an additional wall of the vein, because of the serpentine nature of this type of blood vessel. Then the blood in the vein, or the intravenous fluid being introduced, extravasates into the surrounding tissues, causing swelling, bruising and pain.

When these events occur, it is necessary to start again. Because of these multiple punctures, the patient may: experience more discomfort and anxiety, be subject to an increased chance for infection, and have a decreased number of sites available for immediate intravenous access. Multiple punctures also require additional operator time and increased medical expenses, because of the extra supplies required.

The operator may try to immobilize the vein with his or her fingers. This however is fraught with the danger of the operator puncturing one of his or her own fingers with the needle and being subject to all the attendant risks of contracting blood borne diseases such as hepatitis B and HIV infections as well as bacterial infections at the puncture site.

Many devices have been proposed to immobilize vascular structures in the past. For example, U.S. Pat. No. 5,415,647 to Pisarik describes an immobilizer for blood vessels having grooves of varying sizes to accommodate different diameters of veins. However, like many prior devices that have attempted to immobilize a blood vessel, Pisarik attempts to hold a vein through an individual's epidermis, and, therefore, is not able to hold a blood vessel in place very well.

SUMMARY OF THE INVENTION

It is therefore an object of the present invention to provide a vasculopath for blood vessels that is able to hold a blood vessel in place to allow a hollow needle or tube to be inserted in the blood vessel.

It is another object of the present invention to provide a vasculopath for blood vessels that may be used to hold in place blood vessels having diameters of various sizes.

It is yet another object of the present invention to provide a vasculopath for blood vessels that is capable of directly gripping a blood vessel or gripping a blood vessel through just a few layers of tissue.

According to one aspect of the present invention, there is provided a vasculopath device comprising: a main hinge body; a first arm member pivotably joined to the main hinge body at a proximal end of the first arm member; a first probe holder joined to a distal end of the first arm member; a first elongated probe joined to the first probe holder and extending from the first probe holder in a non-parallel direction to the first arm member; a second arm member pivotably joined to the main hinge body at a proximal end of the second arm member; a second probe holder joined to a distal end of the second arm member; a second elongated probe joined to the second probe holder and extending from the second probe holder in a non-parallel direction to the second arm member; adjusting means for moving the first and second arm members from a starting position to at least one adjusted position and for maintaining the first and second arm at the adjusted position.

According to a second aspect of the present invention, there is provided a vasculopath device comprising: a first arm member; a first probe holder joined to a distal end of the first arm member; a first elongated probe joined to the first probe holder and extending from the first probe holder in a non-parallel direction to the first arm member; a second arm member; a second probe holder joined to a distal end of the second arm member; a second elongated probe joined to the second probe holder and extending from the second probe holder in a non-parallel direction to the second arm member; a spring hinge body for urging the first arm member and the second arm member away from each other, the spring hinge body being fixed to a proximal end of the first arm member and a proximal end of the second arm member; and an adjusting means for moving the first and second arm members from a starting position to at least one adjusted position and for maintaining the first and second arm at the adjusted position.

According to a third aspect of the present invention, there is provided a method for holding a blood vessel comprising the steps of: intradermally inserting two elongated pointed probes parallel to a blood vessel into an individual; and moving the two elongated pointed probes towards each other until they hold the blood vessel in place.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Definitions

For the purposes of the present invention, the term "proximal" refers to a direction towards a user of a vasculopath device. For the purposes of the present invention, the term "distal" refers to a direction away from the user of a vasculopath device.

For the purposes of the present invention the term "individual" refers to either an individual person or animal on whom the method of the present invention is practiced.

For the purposes of the present invention the term "probe free end" refers to an end of an elongated probe that extends from the probe holder holding a probe.

For the purposes of the present invention, the term "blood vessel" includes veins, arteries, capillaries, etc.

Description

Figure 1A:
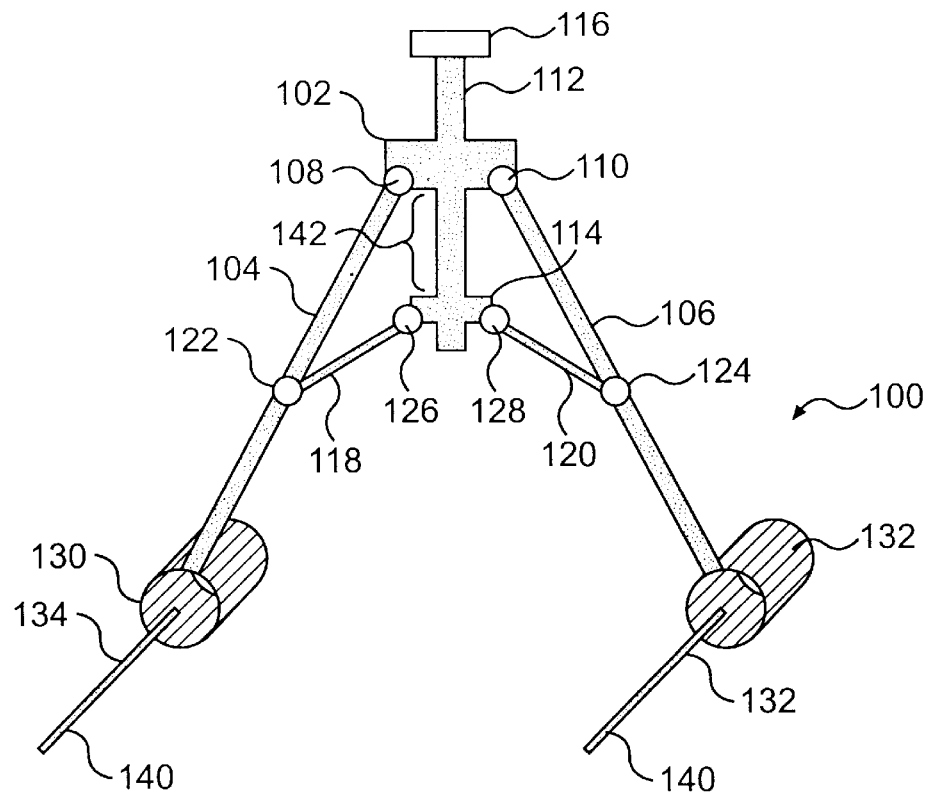
FIG. 1A is a schematic perspective view of a vasculopath device of the present invention.
Figure 1B:
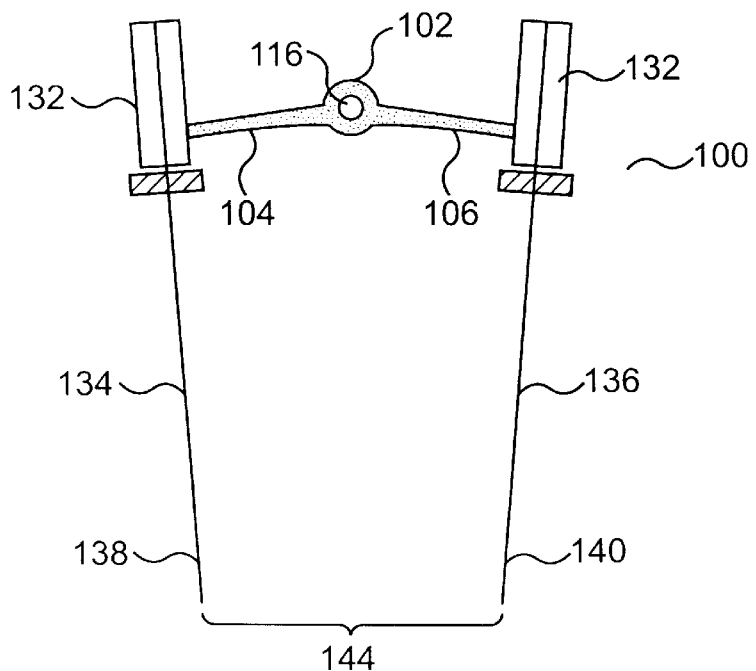
FIG. 1B is a schematic top view of the vasculopath device of FIG. 1B.

FIGS. 1A and 1B illustrate one preferred embodiment of the present invention. A vasculopath device 100 includes a main hinge body 102 and two arm members 104 and 106 that are joined to hinge body 102 at pivots 108 and 110, respectively. An axial screw 112 extends through a threaded opening (not visible in FIGS. 1A and 1B) in main hinge body 102 and through a threaded opening (not visible in FIGS. 1A and 1B) in a supplementary hinge body 114. Screw 112 includes a knob 116 that allows screw 112 to be easily turned by a user of device 100. Supplementary members 118 and 120 are pivotably connected to arm members 104 and 106, respectively, by pivots 122 and 124, respectively. Supplementary members 118 and 120 are also pivotably connected to supplementary hinge body 114 by pivots 126 and 128, respectively. Cylindrical probe holders 130 and 132 are joined to arm members 104 and 106, respectively. Extending from probe holders 130 and 132 are elongated probes 134 and 136. As can be seen in FIG. 1A, elongated probes 134 and 136 extend in directions that are non-parallel to arm members 104 and 106, respectively, to which the elongated probes 134 and 136 are attached by means of probe holders 130 and 132, respectively. Free ends 138 and 140 of elongated probes 134 and 136 are angled towards each other and are pointed, as shown in FIG. 1B.

In the embodiment illustrated in FIGS. 1A and 1B, screw 112 acts as an adjustment mechanism for elongated probes 134 and 136. In order to move elongated probes 134 and 136 towards each other to hold a blood vessel, a user turns knob 116 in a direction to cause screw 112 to be drawn up proximally through supplementary hinge body 114 and main hinge body 102. As screw 112 moves proximally, axial distance 142 between supplementary hinge body 114 and main hinge body 102 lessens and separation distance 144 between elongated probes 134 and 136 lessens. In order to release elongated probes 134 and 136 from blood vessel, a user turns knob 116 in a direction to cause screw 112 to move distally through main hinge body 102 and supplementary hinge body 114. As screw 112 moves distally, axial distance 142 between supplementary hinge body 114 and main hinge body 102 increases and separation distance 144 between elongate probes 134 and 136 increases.

The various pivots of the present invention may be any kind of conventional pivots such as bolts, screws, etc. which are used to join two pieces of metal, plastic, etc. together and allow the two pieces to rotate freely with respect to each other.

Figure 2A:
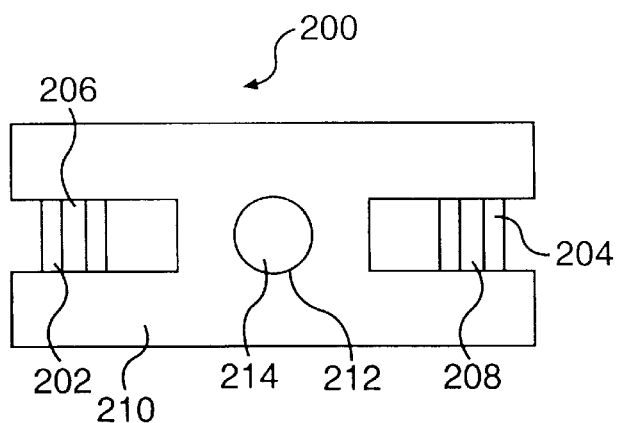
FIG. 2A is a cross-sectional view of a main hinge body of a vasculopath device of the present invention.
Figure 2B:
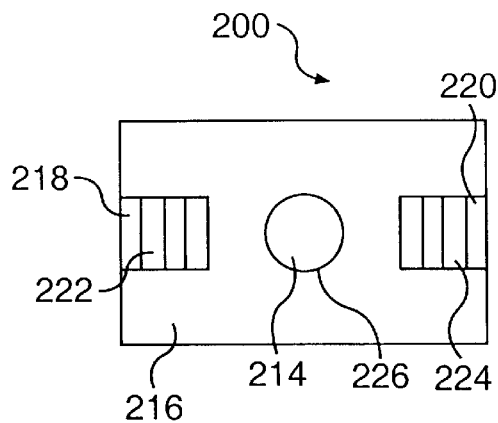
FIG. 2B is a cross-sectional view of a supplementary hinge body of the vasculopath device of FIG. 2A.

Although in the embodiment shown in FIGS. 1A and 1B, the arm members are joined to the hinge body on one side of the main hinge body and the supplementary members are joined on one side of the supplementary hinge body, the present invention also contemplates other arrangements. For example, FIGS. 2A illustrates a vasculopath device 200 of the present invention in which arm members 202 and 204 are mounted on pivots 206 and 208 within a main hinge body 210 having a threaded opening 212 through which a screw 214 extends. Similarly, FIG. 2B illustrates a supplementary hinge body 216 of vasculopath device 200 in which two supplementary members 218 and 220 are mounted on pivots 222 and 224, respectively. Similar to the embodiment shown in FIG. 1A, screw 214 extends through a threaded opening 226 in supplementary hinge body 216.

Figure 3:
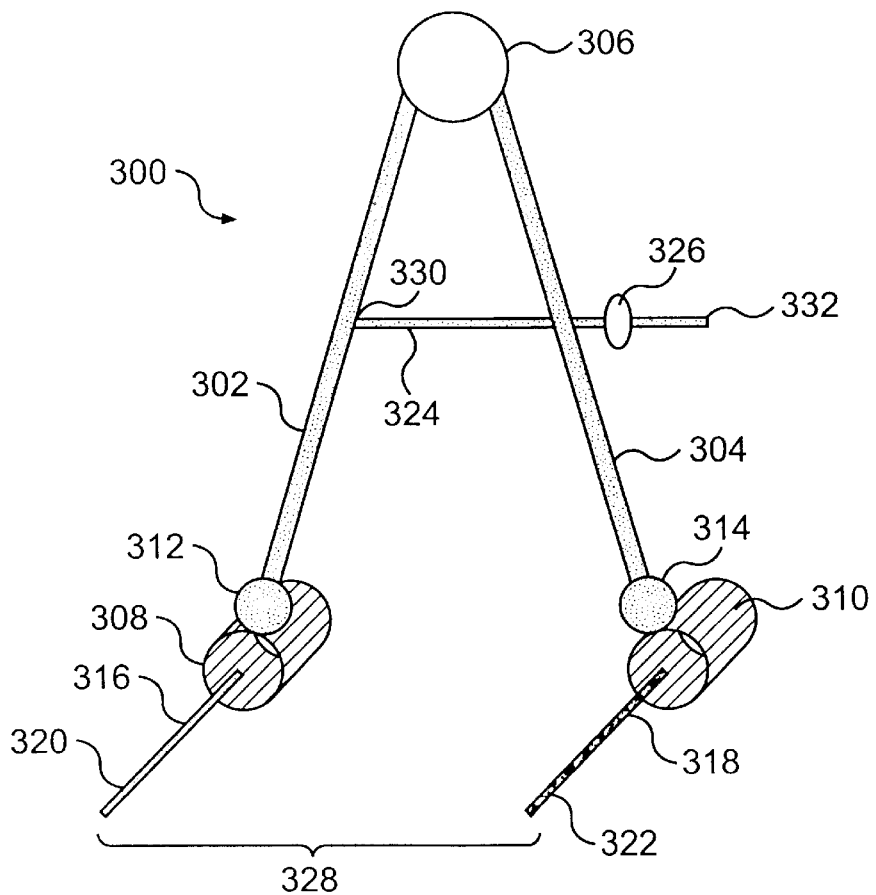
FIG. 3 is a schematic perspective view of a vasculopath device of the present invention.

FIG. 3 illustrates another preferred embodiment of the present invention. A vasculopath device 300 includes a fixed arm member 302 and a moving arm member 304 joined to a main hinge body or circular spring 306. Probe holders 308 and 310 are joined to respective arm members 302 and 304 by universal locking ball joints 312 and 314. Mounted in probe holders 308 and 310 are elongated probes 316 and 318, respectively, having respective pointed free ends 320 and 322. Probe holders 308 and 310 and elongated probes 316 and 318 are similar to the probe holders and probes illustrated in FIGS. 1A and 1B. Locking ball joints 312 and 314 allow probe holders 308 and 310, and therefore, probes 316 and 318 to be pivoted with respect to arm members 302 and 304, respectively, in a variety of directions. Locking ball joints 312 and 314 provide at least some resistance when probe holders 308 and 310 are pivoted so that probe holders 308 and 310 can be maintained at particular orientations which respect to arm members 302 and 304, respectively, without the user being required to hold probe holders 308 and 310 in place. Locking ball joints 312 and 314 are similar to the kind of ball joints used in socket sets.

A lateral screw 324 is fixed to arm member 302 and extends through an opening (not shown) in arm member 304. A stopper 326 travels on screw 308 by means of a threaded opening (not shown in FIG. 3) that extends all the way through stopper 326. The arrangement of lateral screw 324 and stopper 326 is similar to the adjusting mechanism used for adjusting calipers. There are two principal ways that screw 324 and stopper 326 may be used as a mechanism to reduce separation distance 328 between probes 316 and 318. One way to reduce separation distance 328 is to squeeze arm members 302 and 304 together against the resistance of circular spring 306 and then turn stopper 326 on screw 324 towards a fixed end 330 of screw 324 until stopper 326 abuts against arm member 304, maintaining the position of arm member 304 relative to arm member 302. A second way to reduce separation distance 328 is to start out with stopper 326 abutting arm 304 and turning stopper 326 so that stopper travels towards fixed end 330 to force arm member 304 towards arm member 302.

There are also two principal ways to increase separation distance 328 using screw 324 and stopper 326. One way to increase separation distance 328 is to turn stopper 326 so that stopper 326 travels towards a free end 332 of screw 324 while a user squeezes arm members 302 and 304 towards each other. Once stopper 326 reaches a desired position where stopper 326 does not abut arm member 304, such as the position shown in FIG. 3, the user releases arm member 304 thereby allowing arm member 304 to abut stopper 326. A second way to increase separation distance 328 is to turn stopper 326 while stopper abuts arm member 304 a direction so that stopper 326 moves towards free end 332. Once arm member 304 reaches a desired position, the user may stop turning stopper 326.

The parts of the embodiment of the vasculopath device of the present invention shown in FIG. 3 may be modified in a variety of ways. For example, the arm members may meet at a pivot instead of a circular spring and curved telescoping spring, similar to the type of spring used in conventional toenail and hedge clippers, may join the arm member distally from the pivot.

The lateral screw and stopper may be varied in a number of ways as well. For example, the lateral screw may have a thread along a portion of its length or its entire length. Instead of being mounted so that it extends through an opening on one of the arm members, the screw may be mounted on one side of each of the arm members and extend beyond the relaxed position of the moving arm member. In this case, the stopper which travels on the screw is preferably large enough and has a shape adapted so that the stopper can abut the moving arm member and hold the moving arm member in a given position relative to the fixed arm member.

Figure 4:
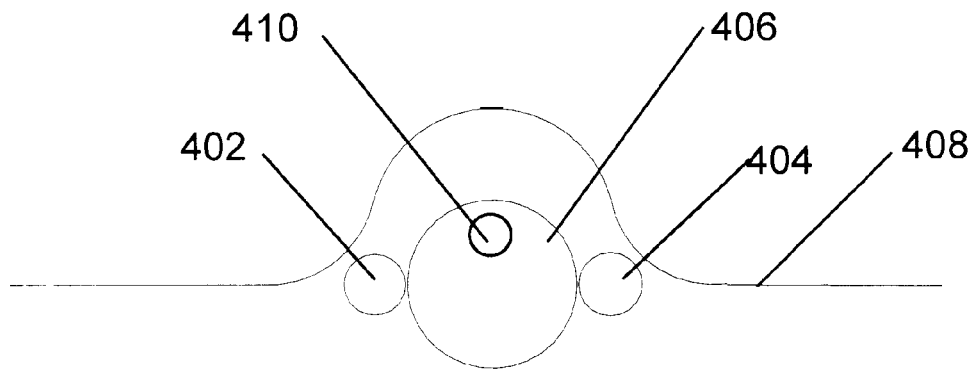
FIG. 4 is a schematic cross-sectional view of probes of the present invention being used to hold a blood vessel in an embodiment of the method of the present invention.

FIG. 4 illustrates one method of how two probes 402 and 404 of a vasculopath device (not shown) of the present invention may be used to hold a blood vessel 406. Probes 402 and 404 are pre-positioned at a separation distance roughly equal to the diameter of blood vessel 406 and then are inserted beneath epidermis 408, i.e. intradermally, and probes 402 and 404 are moved slightly toward each other to hold blood vessel 406 in place. A needle 410 is then inserted into blood vessel 406. Instead of a needle, other devices, such as an intravenous tube may be inserted into the held blood vessel.

Figure 5:
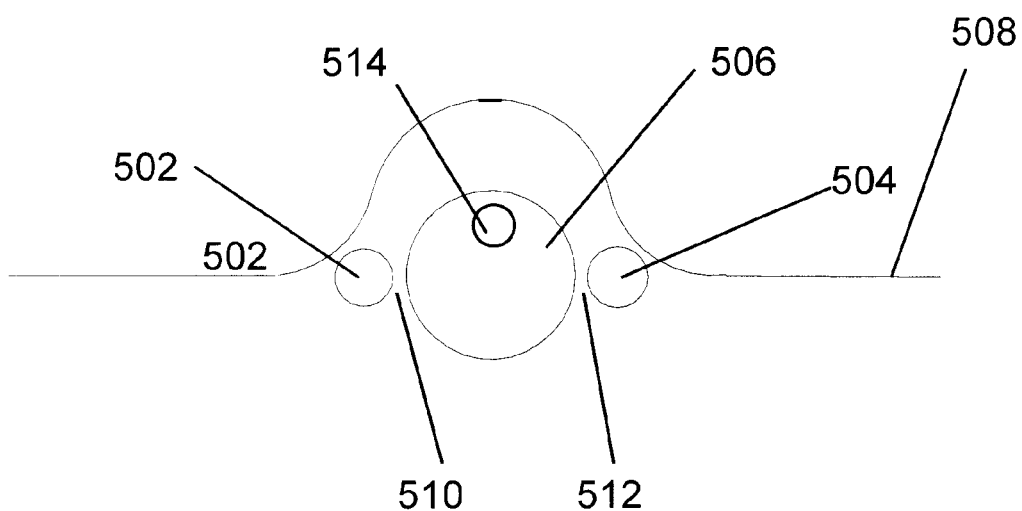
FIG. 5 is a schematic cross-sectional view of probes of the present invention being used to hold a blood vessel in an alternative embodiment of the method of the present invention.

FIGS. 5 illustrates an alternative method of how two probes 502 and 504 of a vasculopath device (not shown) of the present invention may be used to hold a blood vessel 506. Probes 502 and 504 are pre-positioned at a separation distance slightly larger than the diameter of blood vessel 506, are inserted beneath epidermis 508, i.e. intradermally, and then probes 502 and 504 are moved towards each other to hold blood vessel 506 in place. In the method illustrated in FIG. 5, there is typically some tissue 510 and 512 separating probes 502 and 504 from blood vessel 506. A needle 514 is then inserted into blood vessel 506. Instead of a needle, other devices, such as an intravenous tube may be inserted into the held blood vessel.

Although the free ends of the probes described above are pointed to allow for the probes to be inserted intradermally into an individual, the present invention also contemplates probes having blunt ends as well. For example, when the vasculopath device of the present invention used to hold a blood vessel in an opening in an individual's skin, made by either a wound or a surgical incision, it may not be necessary to insert the vasculopath device of the present invention into the individual's skin. Therefore, it may be desirable to use probes having blunt ends to reduce the risk of puncturing the blood vessel being held.

The elongated probes of the present invention may have a variety of lengths, preferably from 2 to 6 cm. The probes may be either solid, similar to a needle, or hollow, similar to a syringe or intravenous tube. The probes are preferably made of a stiff material such as a metal or plastic of the type commonly used in surgical instruments.

The elongated probes of the present invention may either be removably attached to the probe holders or permanently fixed to the probe holders. Preferably each of the probe holders of the present invention is a predominantly solid object with a hole extending partway into the holder into which a probe is fitted, either permanently or removably. Although the probe holders in the embodiments described above are solid cylinders, the probe holders may be any convenient shape that can be used to hold a probe.

The vasculopath device of the present invention is different from prior art methods of providing better access to blood vessels in several important ways. First, the vasculopath may be used to clamp blood vessels intradermally, i.e. below the surface of the skin. Also, because the vasculopath device may be used intradermally, the device is able to hold vessels in a more controlled manner than prior extradermal devices i.e devices which attempt to grip a blood vessel through an individual's skin. In contrast, the elongated probes of the vasculopath device may either grip a blood vessel directly or through just a few layers tissue immediately surrounding a blood vessel. Because of the way that the elongated probes grip a blood vessel, the vasculopath device may be used to aid in arterial cannulation.

The vasculopath device of the present invention may also be used as a vessel clamp. When vessels bleed uncontrollably there are only a limited number of options that may be used to stop the bleeding. Currently, direct pressure is most often employed, but this generally prevents access to the wound, and, therefore, prevents examination. The bleeding vessel may be tied off, but this has fallen out of favor because of the resultant tissue damage. A tourniquet may be applied proximal to the bleeding site, but this typically damages all tissue distal to the tourniquet. In any case, when there is tissue damage as described above, an operation is usually required to fix the bleeding vessel. In contrast the vasculopath device of the present invention is able to clamp a vessel long enough to allow for examination of the surrounding wound, without causing as much tissue damage as is incurred by vessel tying and tourniquet application.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A vasculopath device comprising:

a main hinge body;

a first arm member pivotably joined to said main hinge body at a proximal end of said first arm member;

a first probe holder joined to a distal end of said first arm member;

a first elongated probe joined to said first probe holder and extending from said first probe holder in a non-parallel direction to said first arm member;

a second arm member pivotably joined to said main hinge body at a proximal end of said second arm member;

a second probe holder joined to a distal end of said second arm member;

a second elongated probe joined to said second probe holder and extending from said second probe holder in a non-parallel direction to said second arm member; and an adjusting means for moving said first and second arm members from a starting position to at least one adjusted position and for maintaining said first and second arm members at said adjusted position.

2. The vasculopath device of claim 1, wherein said adjusting means comprises:

a supplementary hinge body located distally of said main hinge body;

two supplementary members, each of said two supplementary members being pivotably joined to said supplementary hinge body and a respective one of said two arm members; and a screw means extending through a first threaded opening in said main hinge body and through a second threaded opening in said supplementary hinge body.

3. The vasculopath device of claim 1, wherein said first elongated probe and said second elongated probe each have a pointed free end.

4. A vasculopath device comprising:

a first arm member;

a first probe holder joined to a distal end of said first arm member;

a first elongated probe joined to said first probe holder and extending from said first probe holder in a non-parallel direction to said first arm member;

a second arm member;

a second probe holder joined to a distal end of said second arm member;

a second elongated probe joined to said second probe holder and extending from said second probe holder in a non-parallel direction to said second arm member;

a spring hinge body for urging said first arm member and said second arm member away from each other, said spring hinge body being fixed to a proximal end of said first arm member and a proximal end of said second arm member; and an adjusting means for moving said first and second arm members from a starting position to at least one adjusted position and for maintaining said first and second arm at said adjusted position.

5. The vasculopath device of claim 4, wherein said adjusting means comprises:

a stopper means;

a rod means on which said stopper travels, said rod means being joined to said first arm member and extending across and beyond said second arm member, said rod means including a first engaging means for engaging a second engaging means on said stopper means so that said stopper means may be held in place at a plurality of positions on said rod means.

6. The vasculopath device of claim 5, wherein said rod means comprises a rod which extends through an opening in said second arm member and includes a screw thread on at least a portion of said rod; said stopper means includes a threaded opening through which said threaded rod extends; said first engaging means comprises said thread on said threaded rod and said second engaging means comprises said threaded opening.

7. The vasculopath device of claim 4, wherein said first elongated probe and said second elongated probe each have a pointed free end.

* * * * *